(12) United States Patent
Attenborough et al.

(10) Patent No.: US 11,491,721 B2
(45) Date of Patent: Nov. 8, 2022

(54) MULTICELLULAR LAY-UP PROCESS

(71) Applicant: Attenborough Dental Laboratories Limited, Nottingham (GB)

(72) Inventors: Edward John Attenborough, Nottingham (GB); Robert Stevens, Nottingahm (GB)

(73) Assignee: Attenborough Dental Laboratories Limited, Nottingham (GB)

( * ) Notice: Subject to any disclaimer, the term of this patent is extended or adjusted under 35 U.S.C. 154(b) by 904 days.

(21) Appl. No.: 16/307,984

(22) PCT Filed: Jun. 8, 2017

(86) PCT No.: PCT/GB2017/051673
§ 371 (c)(1),
(2) Date: Dec. 7, 2018

(87) PCT Pub. No.: WO2017/212282
PCT Pub. Date: Dec. 14, 2017

(65) Prior Publication Data
US 2019/0283325 A1    Sep. 19, 2019

(30) Foreign Application Priority Data

Jun. 9, 2016 (GB) .................... 1610101
Jul. 14, 2016 (GB) .................... 1612253

(51) Int. Cl.
*B33Y 10/00*       (2015.01)
*B29C 64/314*    (2017.01)
(Continued)

(52) U.S. Cl.
CPC .......... *B29C 64/314* (2017.08); *A61L 27/16* (2013.01); *A61L 27/3804* (2013.01);
(Continued)

(58) Field of Classification Search
None
See application file for complete search history.

(56) References Cited

U.S. PATENT DOCUMENTS 4,352,883 A * 10/1982 Lim .................. A61K 9/5073
435/178
6,419,960 B1 * 7/2002 Krishnamurthy .... A61K 9/0053
424/490

(Continued)

FOREIGN PATENT DOCUMENTS

| WO | 2012121874 A1 | 9/2012 |
| WO | 2012148684 A1 | 11/2012 |
| WO | 2012149496 A1 | 11/2012 |

OTHER PUBLICATIONS

International Search Report and Written Opinion of International Application No. PCT/GB2017/051673, md dated Nov. 28, 2017, 16 pages.
(Continued)

*Primary Examiner* — Mohammad M Ameen
(74) *Attorney, Agent, or Firm* — Maine Cernota & Rardin (57) ABSTRACT

Disclosed herein is a multicellular lay-up process. The process comprises the steps of: a) forming a core material, b) forming a capsule material, c) encapsulating the core with the capsule material, d) adding the capsule to a substrate, and e) exposing the capsule to at least one bioactivating agent.

32 Claims, 11 Drawing Sheets

(51) Int. Cl.
*B33Y 40/00* (2020.01)
*B33Y 70/00* (2020.01)
*B29C 64/10* (2017.01)
*A61L 27/16* (2006.01)
*A61L 27/38* (2006.01)
*A61L 27/52* (2006.01)
*A61L 27/54* (2006.01)
*A61L 27/58* (2006.01)
*C12N 5/00* (2006.01)
*C12N 5/071* (2010.01)
*D01D 5/00* (2006.01)

(52) U.S. Cl.
CPC ....... *A61L 27/3834* (2013.01); *A61L 27/3891* (2013.01); *A61L 27/52* (2013.01); *A61L 27/54* (2013.01); *A61L 27/58* (2013.01); *B29C 64/10* (2017.08); *B33Y 10/00* (2014.12); *B33Y 40/00* (2014.12); *B33Y 70/00* (2014.12); *C12N 5/0062* (2013.01); *C12N 5/0602* (2013.01); *D01D 5/003* (2013.01); *A61L 2300/404* (2013.01); *A61L 2300/41* (2013.01); *A61L 2300/414* (2013.01); *C12N 2501/10* (2013.01); *C12N 2513/00* (2013.01)

(56) References Cited

U.S. PATENT DOCUMENTS

| | | | |
|---|---|---|---|
| 2002/0090725 A1* | 7/2002 | Simpson | D01F 1/10 435/402 |
| 2008/0286323 A1* | 11/2008 | Tomoe | A61P 25/00 424/423 |
| 2010/0221304 A1 | 9/2010 | Tan et al. | |
| 2011/0024035 A1* | 2/2011 | Koplin | B01J 13/02 156/275.7 |
| 2012/0213708 A1* | 8/2012 | Anderson | A61K 9/0019 424/9.2 |
| 2014/0271843 A1* | 9/2014 | Ma | A61K 9/5078 424/463 |

OTHER PUBLICATIONS

Garret D. Nicodemus et al: "Cell Encapsulation in Biodegradable Hydrogels for Tissue Engineering Applications", Tissue Engineering Part B: Reviews, vol. 14, No. 2, Jun. 1, 2008, pp. 149-165, XP055143263.

Search Report under Section 17(5) of Great Britain Patent Application No. GB1612253.3, md dated Feb. 21, 2018, 4 pages.

\* cited by examiner

Deposition of dry hydrophobic particles (e.g. PTFE)

Figure 8

Irrigation of Thawed Cryo Biocapsules using aqueous solutions (>0C) which are doped with bioactive agents.

Bioreactor culture
- Tray becomes part of a bioreactor.
- Shell releases Bioactive Nanofibre agents to promote cell attachment.
- Slow release of bioactive factors from fibre induce cell differentiation in the microenvironment.
- Porous hydrophobic particles promote exchange of respiration gases
- Hydrogel additives (Trehalose) reduced to glucose by Trehalase..

MULTICELLULAR LAY-UP PROCESS

RELATED APPLICATIONS

This application is a national phase application filed under 35 USC § 371 of PCT Application No. PCT/GB2017/051673 with an International filing date of Jun. 8, 2017, which claims priority of GB Patent Application 1610101.6 filed Jun. 9, 2016 and GB Patent Application 1612253.3 filed Jul. 14, 2016. Each of these applications is herein incorporated by reference in its entirety for all purposes.

FIELD OF THE INVENTION

The present invention relates to a multicellular lay-up process.

BACKGROUND TO THE INVENTION

Tissue engineering holds great promise for trauma repair, regeneration of tissue after injury or disease, or even building up whole organs. Skin grafts are now regularly grown in vitro for transplanting onto patients with burns injuries or for repairing large skin areas. It is also possible to grow whole bladders in vitro, as well as other tissues such as cartilage and bone. One of the problems faced by scientists is how to regenerate tissues where there is not only a requirement for large numbers of cells, but also a requirement for many cell types.

Large numbers of cells, require large amounts of nutrients, which is problematic not only in the in vitro growth phase, but after transplanting into the patient. This problem has been addressed partially for some tissues, and skin is a good example where this type of engineering has had some success. It is now possible to spray stem cells onto a patient to repair skin damage. The technology requires a device that sprays a patient's own self-donated (autologous) stem cells to treat burns and other wounds. The method is used in conjunction with a technique that isolates adult stem cells for application to the wound site, where they differentiate into normal skin. This treatment can replace conventional methods of treating severe wounds, such as skin grafting. Studies demonstrate that damaged skin tissue regenerates after skin gun treatment significantly more quickly than after traditional treatment methods, and this is primarily because large numbers of living viable cells are delivered straight to the required area. Unfortunately this technology has not been extended to include the regeneration of skin lost due to other injuries or skin diseases and it is also limited in that it is only effective immediately following the burn incident. One advance on this type of technology is to print skin cells onto burn wounds. The "ink" is actually different kinds of skin cells. A scanner is used to determine wound size and depth. Different kinds of skin cells are found at different depths. This data guides the printer as it applies layers of the correct type of cells to cover the wound.

Another technique that is used to deliver large numbers of cells to a target area is microencapsulation. Cell microencapsulation technology involves immobilization of the cells within a polymeric semi-permeable membrane that permits the bidirectional diffusion of molecules such as the influx of oxygen, nutrients, growth factors etc. essential for cell metabolism and the outward diffusion of waste products and therapeutic proteins. At the same time, the semipermeable nature of the membrane prevents immune cells and antibodies from destroying the encapsulated cells regarding them as foreign invaders. The potential of using cell microencapsulation in successful clinical applications can be realized only if several requirements encountered during the development process are optimized such as the use of an appropriate biocompatible polymer to form the mechanically and chemically stable semi-permeable matrix, production of uniformly sized microcapsules, use of an appropriate immune-compatible polycations cross-linked to the encapsulation polymer to stabilized the capsules, selection of a suitable cell type depending on the situation. The main motive of cell encapsulation technology is to overcome the existing problem of graft rejection in tissue engineering applications and thus reduce the need for long-term use of immunosuppressive drugs after an organ transplant to control side effects.

With regard to diabetes, the potential of using bioartificial pancreas, for treatment of diabetes mellitus, based on encapsulating islet cells within a semi permeable membrane is extensively being studied by scientists. These devices could eliminate the need for of immunosuppressive drugs in addition to finally solving the problem of shortage of organ donors. The use of microencapsulation would protect the islet cells from immune rejection as well as allow the use of animal cells or genetically modified insulin-producing cells. It is hoped that development of these islet encapsulated microcapsules could prevent the need for the insulin injections needed several times a day by type 1 diabetic patients. However, the two major hurdles faced in this technique are the limited availability of donor organs and with the need for immunosuppresents to prevent an immune response in the patient's body. The polymers used for islet microencapsulation are alginate, chitosan, polyethylene glycol (PEG), agarose, sodium cellulose sulphate and water-insoluble polyacrylates with alginate and PEG being commonly used polymers. However, there are still several major issues such as biocompatibility and immunoprotection need to be overcome.

The use of cell encapsulated microcapsules towards the treatment of several forms of cancer has shown great potential. One approach undertaken by researchers is through the implantation of microcapsules containing genetically modified cytokine secreting cells. An example of this was demonstrated when genetically modified IL-2 cytokine secreting non-autologous mouse myoblasts implanted into mice showed a delay in the tumour growth with an increased rate of survival of the animals. However, the efficiency of this treatment was brief due to an immune response towards the implanted microcapsules. Another approach to cancer suppression is through the use of angiogenesis inhibitors to prevent the release of growth factors which lead to the spread of tumours. The effect of implanting microcapsules loaded with xenogenic cells genetically modified to secrete endostatin, an antiangiogenic drug which causes apoptosis in tumour cells, has been extensively studied. However, this method of local delivery of microcapsules was not feasible in the treatment of patients with many tumours or in metastasis cases and has led to recent studies involving systemic implantation of the capsules.

Numerous studies have been dedicated towards the development of effective methods to enable cardiac tissue regeneration in patients after ischemic heart disease. An emerging approach to answer the problems related to ischemic tissue repair is through the use of stem cell-based therapy. However, the actual mechanism due to which this stem cell-based therapy has generative effects on cardiac function is still under investigation. Even though numerous methods have been studied for cell administration, the efficiency of the number of cells retained in the beating heart after implantation is still very low. A promising approach to overcome this problem is through the use of cell microencapsulation therapy which has shown to enable a higher cell retention as compared to the injection of free stem cells into the heart.

Even with all the above studies, there are still problems with rejection, how to lay down multiple cell types in the same place as might be found in a complex organ or body part, and how to retain the capsule in the right place.

The inventors have now designed a multicellular lay-up process which overcomes the above referenced short comings associated with the prior art.

SUMMARY OF THE INVENTION

In one aspect of the invention there is provided a multicellular lay-up process, the process comprising the steps of:
a) forming a core material,
b) forming a capsule material,
c) encapsulating the core with the capsule material,
d) adding the capsule to a substrate,
e) exposing the capsule to at least one bioactivating agent.

The present invention is advantageous primarily because it means that the core material is maintained in a more stable manner than any conventional methods. Thus the material of the core remains viable for longer and under more extreme environmental conditions. Furthermore the method provides a process for laying up core material on a substrate allowing the ability to selectively activate various regions or parts of the core material on said substrate.

It will be appreciated that the method of the invention is not restricted to the singular, and therefore preferably, the method comprises forming a plurality of capsules, adding a plurality of capsules to a substrate and exposing the plurality of capsules to at least one bioactivating agent. This allows for variety of construction.

Preferably the core comprises one or more mammalian cells, cell culture medium and a hydrogel. This allows the method to be used where the core material includes cellular material and by forming the core as described the cellular material is held in a stable and viable environment. Where the core comprises mammalian cells it means that the method can be used to lay-up cells on a substrate, which can then be grown in culture to form either a tissue or an organ or simply further generations of the cells. Such growth is more efficient than in conventional methods, due to the improved storage environment of the cells in the core and the capsule.

Preferably cells are stem cells. This allows, the lay-up of stems cells on a substrate which can then be used to generate many different types cells, which when cultured can grow into tissues or organ, depending on the type of differentiation they are directed towards. The cells may also be the patient's own cells, autologous cells or mixtures of the above.

Preferably, the cell culture medium comprises selective growth medium, growth factor or buffer. This allows for a ready supply of nutrients for the cells once they start to grow on the substrate.

Preferably the hydrogel comprises any of gelatin, polyethylene glycol, glycerol, alginate, dextran-40, trehalose, or DMSO. These materials are cryoprotectants and protect the cellular material during frozen storage. The hydrogel provides cushioning to the cells and helps to transfer gasses to and from the cells when they are in culture.

The core may further comprises at least one bioactivating agent selected from the group consisting of growth factors, growth inhibitors or growth selectors. This has the benefit that when the cells start their culture cycle on the substrate, the bioactivating agent is readily available and therefore there is no delay in the differentiation or growth patterns that the agents promote.

Preferably the step of forming the core comprises combining one or more mammalian cells, at least one bioactivating agent, cell culture medium and a hydrogel. The combining may be simple mixing or additive combination.

Preferably the capsule material comprises a water soluble polymer, a fibrous component, and a solvent. This mixture stabilises the core material and makes it useable. That is to say it can then be transported, frozen, handled etc. The capsule material also, once formed around the core buffers the shear stresses exerted on the core and on the cells in the core but forces exerted in transport or mixing. These stresses might otherwise stimulate the cells to differentiate incorrectly. The properties of the capsule formulation aid electrohydrodynamic formation of core-capsule structures.

Preferably the water soluble polymer comprises polyethylene oxide [PEO] and/or polyethylene glycol [PEG]. When the cells are in the culture environment the PEO and/or PEG goes to make a hydrogel which aids cell culture. Other suitable water soluble polymers include polyvinyl pyrrolidone, polyvinyl alcohol, polyacrylic acid, polyacrylamide, polyphosphates, Xanthan Gum, Pectins, Chitosan Derivatives, Dextran, hyaluronic acid, albumin, starch and starch based derivatives, alginate, Gelatin, Chitosan, Collagen, Agarose or Cellulose Sulphate and their co-polymers.

Preferably the fibrous component comprises cryomilled nanofibres, cryo-sonic milled fibres, or lithographic cut bioactive nano fibres. The fibres allows the construction of the capsule which would otherwise disintegrate. The milling segments the fibres. The 'fibre segmentation' procedure also mills the fibres to lengths and sizes within a particular range. Therefore the viscosity of the capsule is controlled. This is important as the capsules need to hold the cores, but also release them when in the culture environment.

Preferably the fibres comprise natural and/or synthetic polymers. The fibres aid formation of the extra cellular matrix material when the cells are in the culture environment. This can speed up any tissue mass generation process.

Preferably the natural polymers comprise cross-linked collagen and or cross linked hyaluronic acid. Preferably the synthetic polymers comprise any of poly lactide glycolic acids, poly lactic acid, poly glycolic acid, or polycapralactone.

Preferably the fibrous component is infused with an enzyme. The enzyme, which may be trehalase for example, breaks down the complex molecules of the hydrogel into sugars such as glucose which are then made ready available to the culturing cells.

Preferably the fibrous component is infused with an electromagnetic absorber. Examples of suitable electromagnetic absorbed include but are not limited to carbon black, graphene nanoflake, quantum dots, or nanoparticules. These additives aid controlled heating of the fibre to heat the cellular microenvironment and to aid release of bioactive agents within or attached to the fibre.

Preferably the solvent comprises water, organic solvents and mixtures of water and organic solvents (e.g. DMSO). This provides suitable viscosity, and volatile fluid for the core material.

Preferably the capsule material further comprises at least one bioactivating agent selected from the group consisting of group consisting of growth factors, growth inhibitors, antimicrobial or anti-inflammatory agents. If an enzyme is stored in the capsule coating its target would generally be stored in the core. This has the same effect as the same agent in the core material.

Preferably the step of encapsulating the core with the capsule material comprises electrospraying both the formed cores and the capsule material concentrically in a cryogenically cooled drop tower. This has the effect that the core material and the capsule material come together at the end of the concentric tube assembly. The environment also has a very low dew point to aid evaporation of the water from the surface. Electrostatic charges induced on the surface of the aid the capsule dripping mode. When the core-shell capsules are falling through a cryo-vapour cooled drop tower the majority of the solvents in the capsule are removed. The solvent evaporation reduces the temperature of the capsule which in turn increases viscosity and increases surface tension. At this stage illumination with electromagnetic radiation could be used to control the capsule formation process. As the capsules continue to fall they are cooled further by a cryogenic vapour which drops the temperature below the glass transition temperature of water (<−135 C). The capsules fall onto a surface which may be inclined to reduce shock impacts. The result is a cryo biocapsule powder at a temperature of less than −135 C where the cells inside are still viable.

Preferably the step of adding the capsule to the substrate is performed in an additive manufacturing process. This means that the addition of the capsules to the substrate can be controlled and the pattern of addition applied from a predetermined pattern. That is to say if one wanted to produce a disc or a rectangular shape they could. As will be described later, preferably a fluidised bed of the capsules is created with the capsules fluidised in a liquid nitrogen vapour. The vapour containing the capsules is then extracted and mixed with warm dry air and direct towards the substrate, at which point the capsules are deposited on the substrate. In this process there is controlled heating of the capsule either by the thermal radiation from a heated delivery tube or by illumination from emission sources with a wavelength which matches the electromagnetic absorbers incorporated in the capsule. The thermal management of the capsule delivery path ensures the capsules are deposited on the substrate above 0 C, typically 4 C.

Preferably the additive manufacturing process is any of high speed sintering, ink jet printing, poly jet printing, spraying, high resolution deposition, spraying, syringe dispensing, near field electrospray or aero-sol jetting. These methods provide for localised addition of capsules (and other components) to a substrate.

Preferably, the adding step further comprises the deposition of a barrier on the substrate. Preferably the barrier comprises dry hydrophobic particles. These may be delivered in a volatile hydrophobic biocompatible solvent. (e.g. Fluorinert). The barrier stops groups of capsules from mixing with one another on the same substrate but also stops any liquid which is subsequently placed on the capsules and on the substrate from transferring from one group of capsules to the other. Therefore the correct bioactivators are kept with right cellular contents.

Preferably the hydrophobic particles comprise PTFE particles. Preferably the deposition of dry hydrophobic particles on the substrate is by any of high speed sintering, ink jet printing, poly jet printing, spraying, high resolution deposition, spraying, syringe dispensing, near field electrospray or aero-sol jetting.

Preferably the step of exposing the capsule to at least one bioactivating agent comprises irrigating the capsules with an aqueous solution comprising one or more bioactivating agents. This is preferably done by any of ink jet printing, poly jet printing, spraying, high resolution deposition or aerosol jetting. The formulations which are deposited using these methods may contain electromagnetic absorbers and/or bioactive agents. The carrier solvent would be typically water or mixtures of water and organic solvents (e.g DMSO). The electromagnetic energy, which is within the absorption band of the electromagnetic absorber is generally converted to produce a heating effect. This heat can raise the temperature of the cellular microenvironment which initiates cellular metabolic activity at the selected sites defined by the location of the absorber.

Preferably the source of the electromagnetic radiation will be a laser, light emitting diode or specialised near infra-red emission sources.

When near infra-red light is shone into the substrate after a layer of capsules has been laid down on the substrate it means that they can be warmed up evenly over the layer thickness of the deposition of capsules. Therefore all the cells are activated at once. Although all deposited cells may be activated if the multilayers of cells are not too thick.

Preferably the one or more bioactivating agents are selected from the group consisting of group consisting of growth factors, growth inhibitors, antimicrobial agents and anti-inflammatory agents.

Preferably steps d) and e) are repeated consecutively in order to layup a three dimensional array of capsules. This means that cells can be cultured in mass groups to create solid three dimensional structures and tissues and organs.

Preferably the capsules that are formed are between 20□m and 50□m in diameter.

Preferably a plurality of capsules comprising cell types programmed to produce a first tissue type are laid down on the substrate adjacent to a plurality of capsules comprising cell types programmed to produce a second tissue type. Therefore on the same substrate one might have two groups of cells next to one another. This means that one type of tissue can be cultured next to another type of tissue. The type of tissue is dependent on the cell type and the activators used.

Also, a plurality of capsules comprising cell types programmed to produce a first tissue type may be laid down on the substrate interposed with a plurality of capsules comprising cell types programmed to produce a second tissue type. This means that one type of tissue can be cultured within another. For example blood vessels within a bone.

The core, capsule material or fibrous component may further comprise a near infrared absorber. This has two benefits. First it means that greater control of the heating process can be obtained when the capsules are deposited onto the substrate from the fluidised bed. This is achieved by shining an infrared light on the supply nozzle. The second benefit is that if infra-red light is shone into the substrate after the capsules have been laid down on the substrate and laid down to various depths, it means that they can be warmed up evenly over the entire thickness of the deposition of capsules. Therefore all the cells are activated at once.

BRIEF DESCRIPTION OF THE DRAWINGS

The invention will now be described by way of example and/or illustration only with reference to the accompanying drawings in which.

DETAILED DESCRIPTION OF THE ILLUSTRATED EMBODIMENT

An embodiment of the invention will now be described by way of example.

Core Formation

Figure 1:
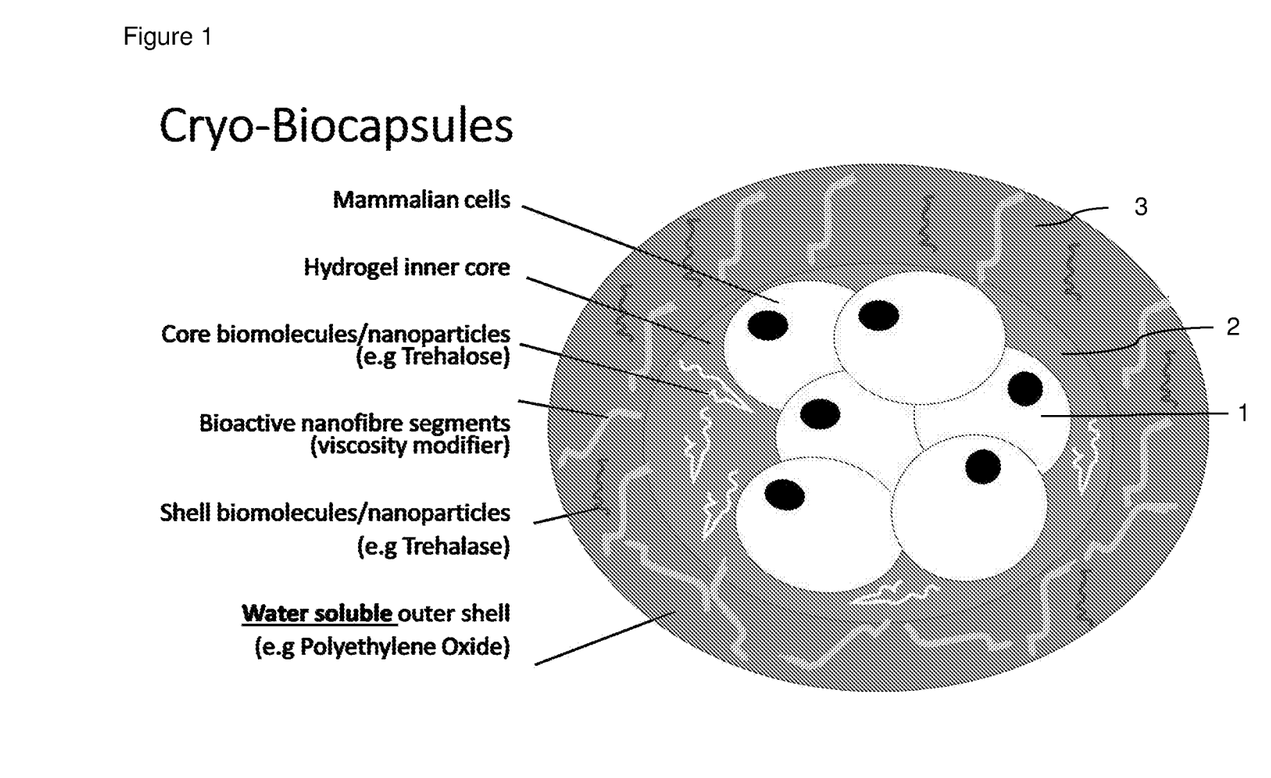
FIG. 1 is a cross-section of an embodiment of the capsule manufactured according to an embodiment of the method of the invention.

A core material was formed by mixture of stems cells (1), with a cell culture media, cryo protectants and bioactive agents (2). The mixing was performed under sterile conditions. See FIG. 1 for a representation of the core within the capsule 3.

Generation of Nano Fibre Segments

Figure 2:
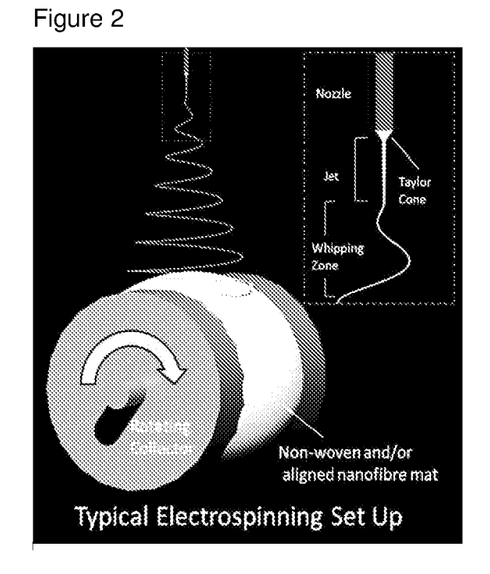
FIG. 2 shows and example of the electro spinning set up used in the invention.
Figure 3:
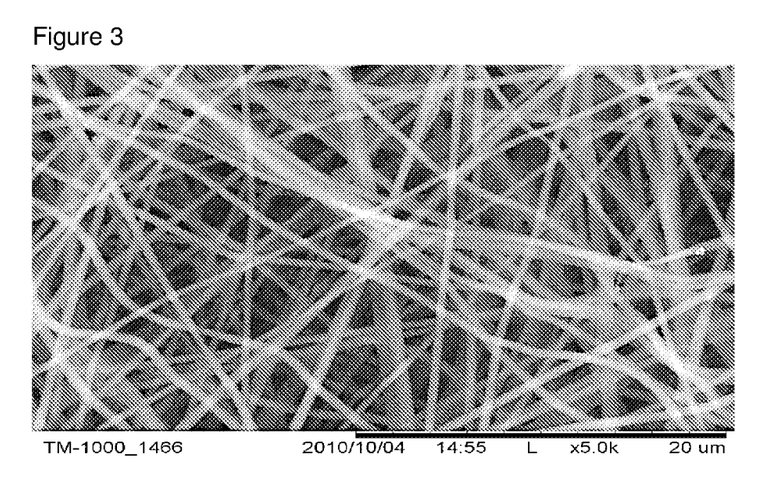
FIG. 3 shows an SEM image of the fibre mat.
Figure 4:
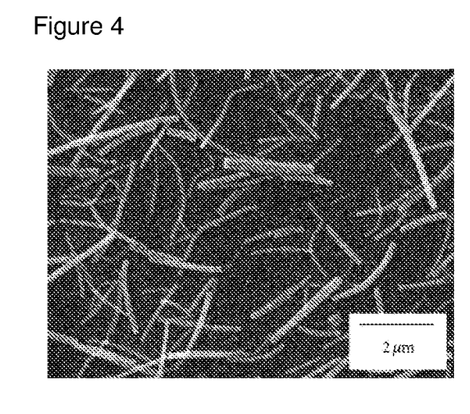
FIG. 4 shows and SEM image of the cryomilled fibre mat.

Using a typical electro spinning apparatus (see FIG. 2) a non-woven mat of poly lactic-co-glycolic acid [PLGA] was produced (FIG. 3). As an example an electrospinning solution of 6 wt % PLGA polymer (Purac) dissolved in Hexafluoroisopropanol (HFIP) was mixed with an aqueous solution of 20 microgrammes of lyophilized growth factor in 333 microlitres of 5 mM TRIS (pH 7.6) containing 0.1% Bovine Serum Albumin). The solution was loaded into poly propylene syringe which is connected to a stainless steel 21 Gauge blunt end tube by PTFE tubing. The tube was connected to a high voltage supply. The temperature of the electrospinning solution was maintained below 37 C. The environment between the electrospinning needle electrospinning solution was controlled so that the relative humidity and the ambient temperature did not vary. Typical values were an RH of 60% and a temperature of 25 C. A rotating collecting drum which had a conductive surface was positioned at a distance of 300 mm from the open end of the stainless steel tube. The surface of the drum was biased at a voltage between 0 kV and −12.5 kV. The stainless steel tube was biased at 10 kV to 30 kV. The electrospinning solution was pumped at a controlled rate (1 mL/hour) through the tube. Electrostatic forces acting on the solution emerging from the end of the tube caused a cone and jet to form. The rheological properties and the molecular weight of the PLGA resulted in entanglement as solvent was lost from the surface of the solution. This resulted in fibre formation. Electrostatic charge density increased as the fibre moved toward the collector drum. The electrostatic forces arising caused elongational extension of the fibre such that micron and nanoscale fibres could be produced. There was a random flight of the fibre between the tube and the collector and this resulted in lay down of a random nanofibre mat of the rotating collector. After a defined time the mat was removed and allowed to dry to ensure all solvents were removed. Then a PEG and/or PEG solution was applied and allowed to dry. The weight ration of the PEG and/or PEG polymer to the weight of nanofibre was controlled. The dry mat was then cryomilled to create particles infused with short fibres (FIG. 4).

Capsule Material Generation

The capsule material was then formed by dissolving the particles produced in water to create the capsule material formulation. For a PEO polymer with a Molecular Weight of 2,000,000 of PEO a 2 wt % ratio of particles to water was used.

Encapsulation of the core with the capsule material.

Figure 5:
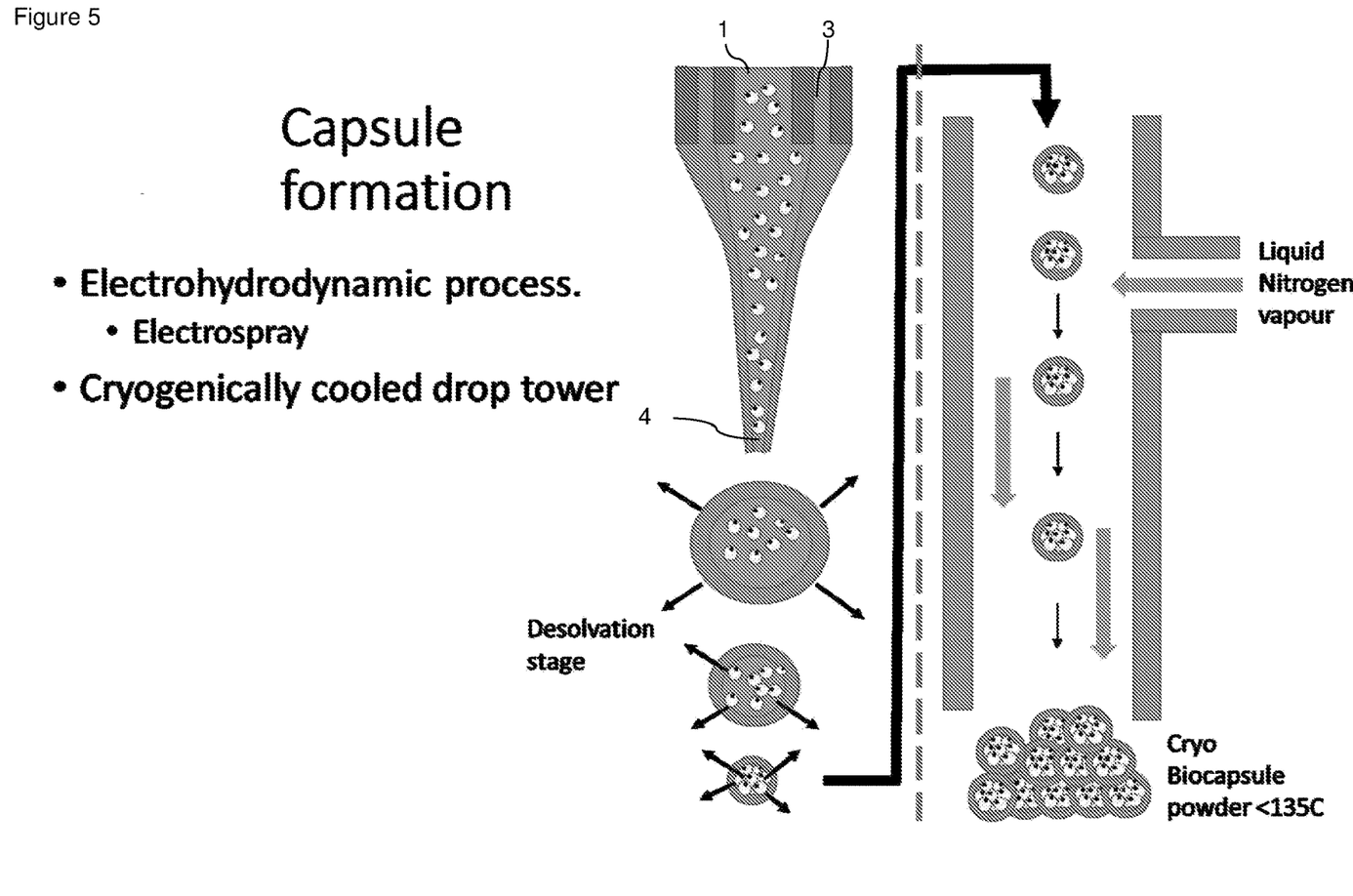
FIG. 5 shows a schematic of an embodiment of the method of forming the capsules around the core.
Figure 6:
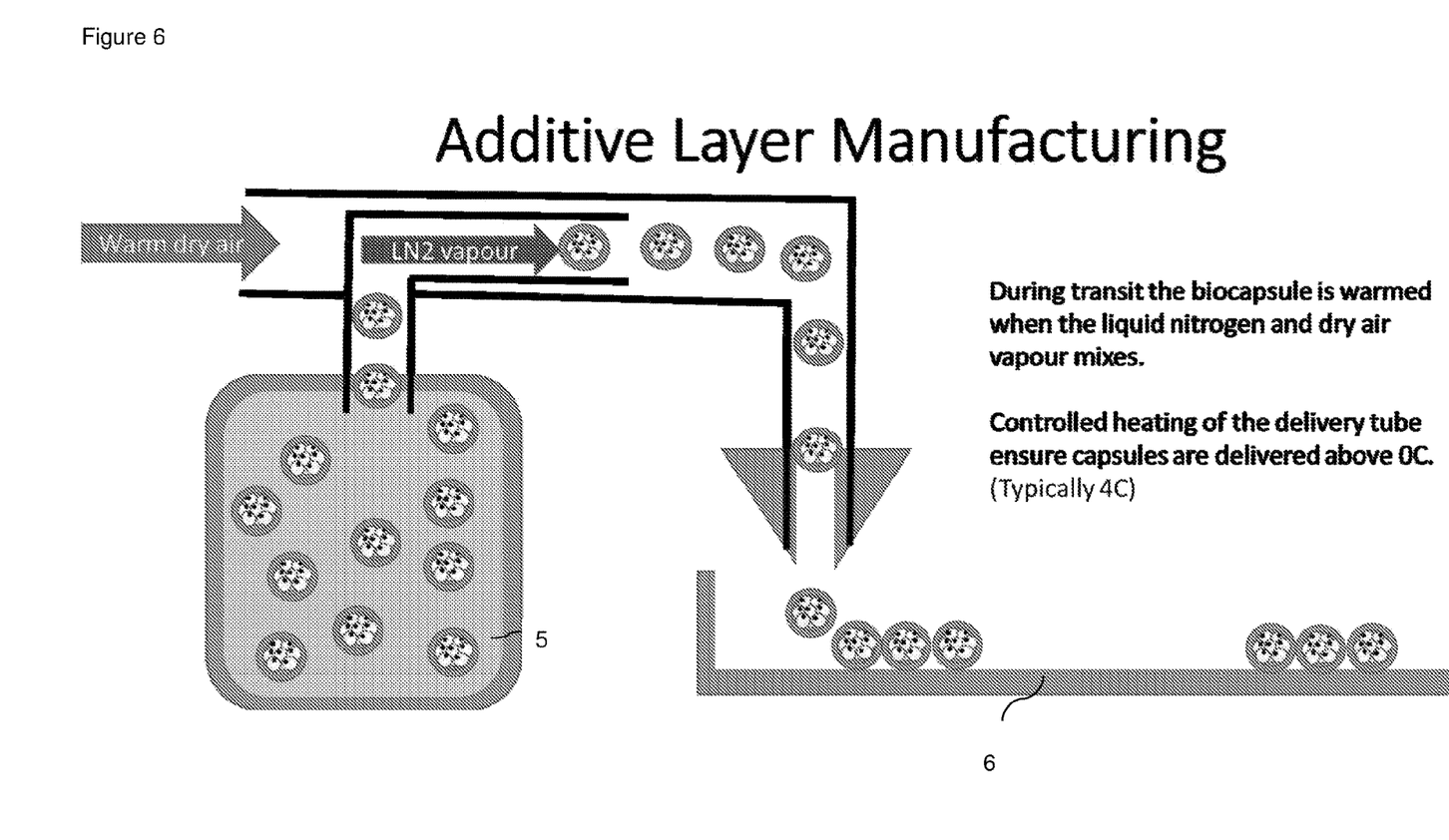
FIG. 6 shows a schematic of an embodiment of the additive layer manufacturing method.
Figure 7:
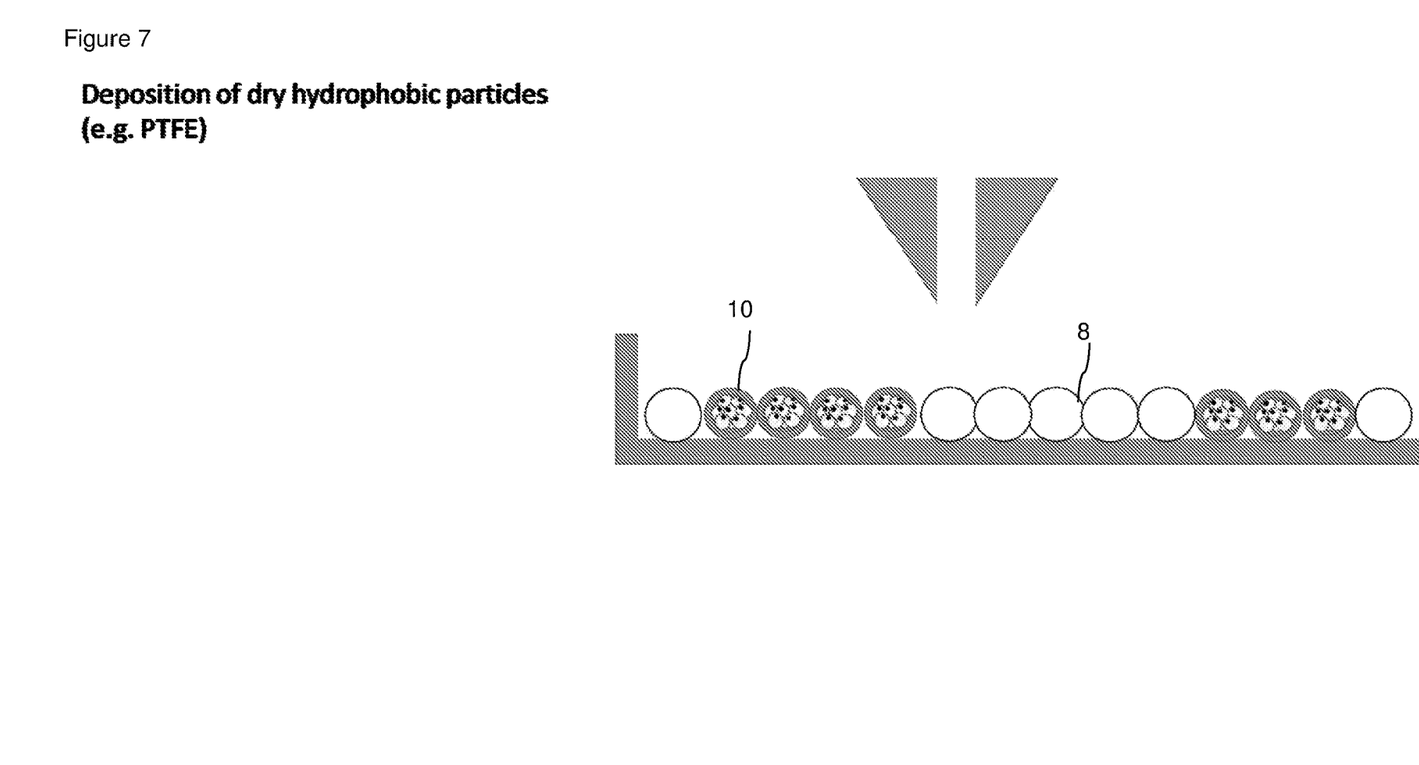
FIG. 7 shows a schematic of an embodiment of the method of addition of barrier materials to the substrate.
Figure 8:
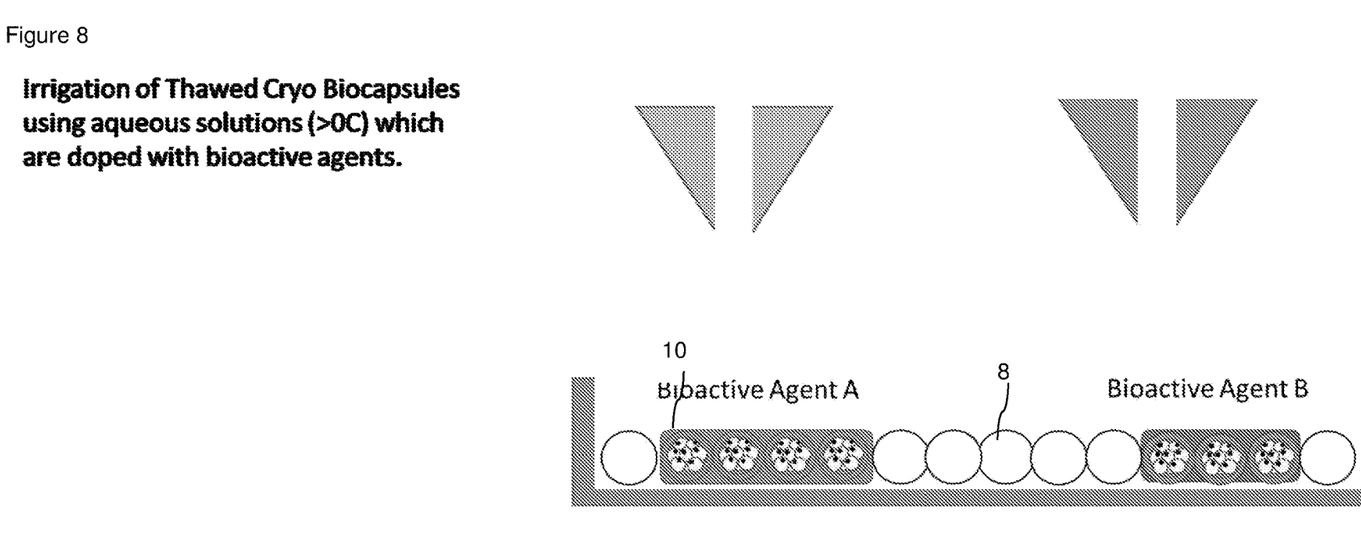
FIG. 8 shows the irrigation of thawed cryo capsules with solutions.
Figure 9:
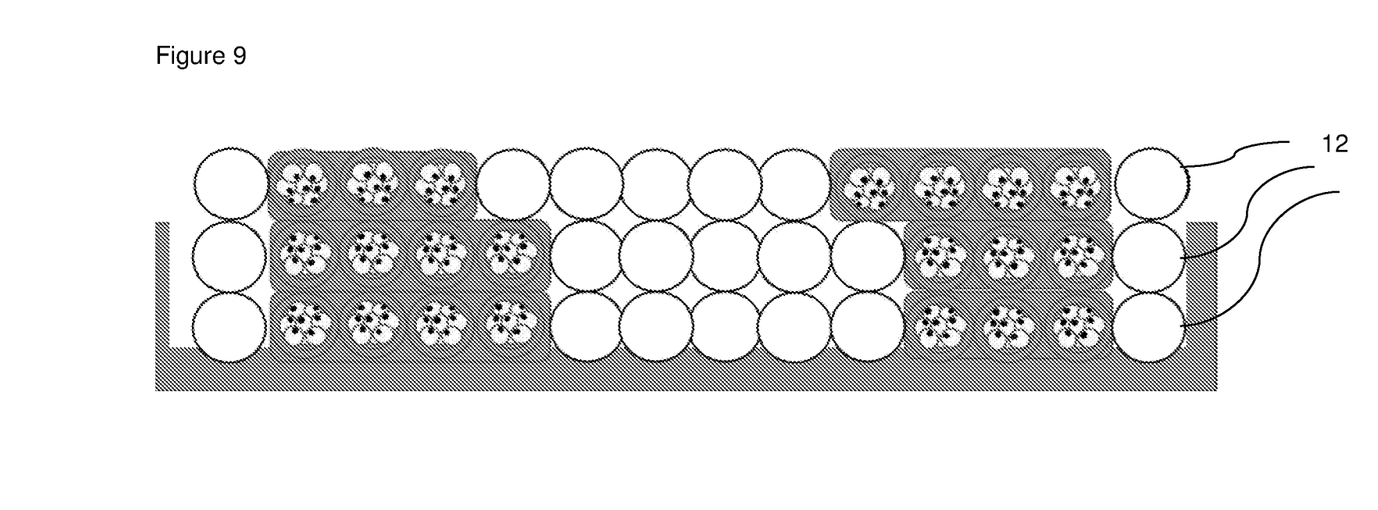
FIG. 9 shows a cross section of the results of an embodiment of the method where steps D and e are repeated.
Figure 10:
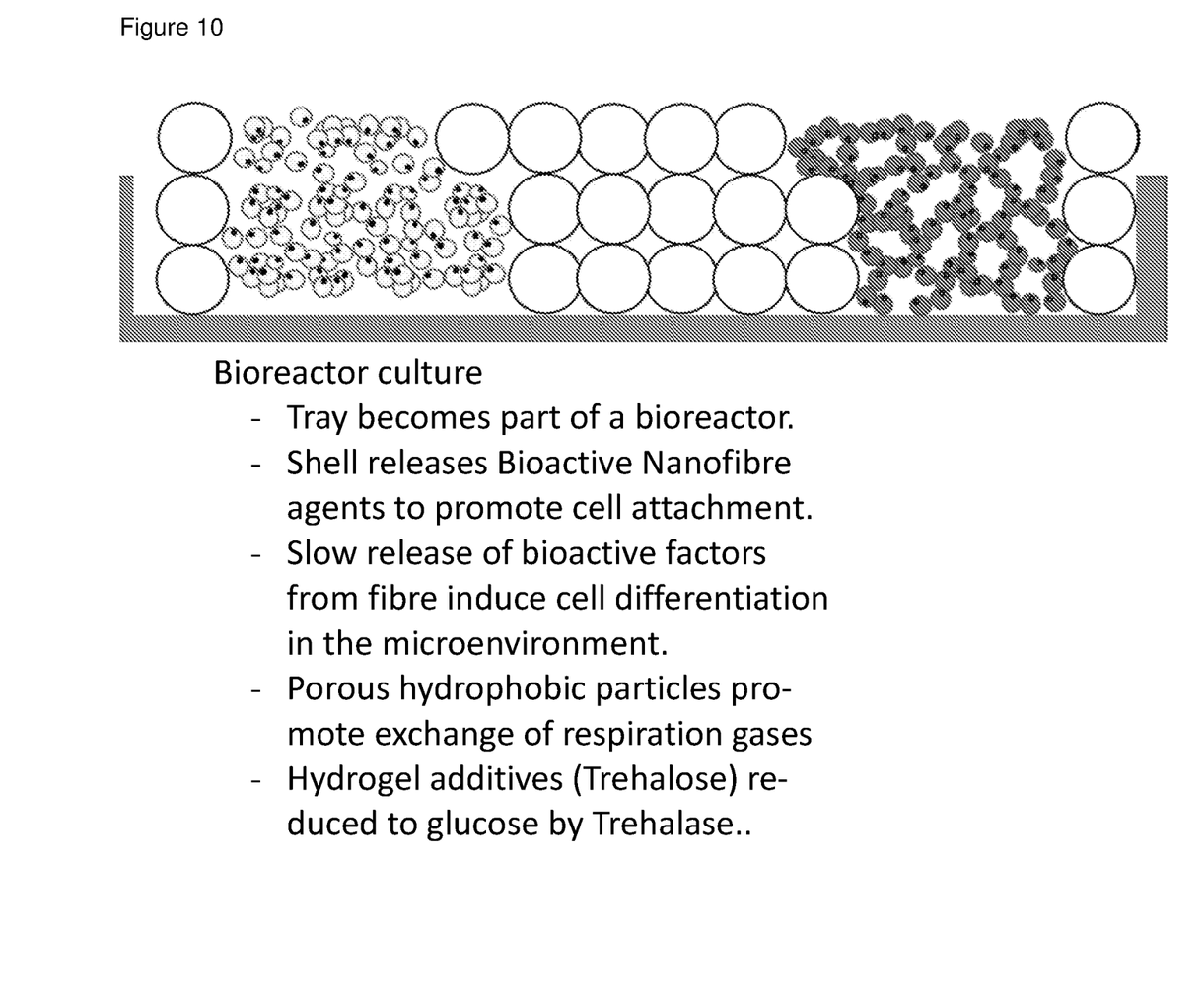
FIG. 10 shows the resultant tissue/organ bioreactor
Figure 11:
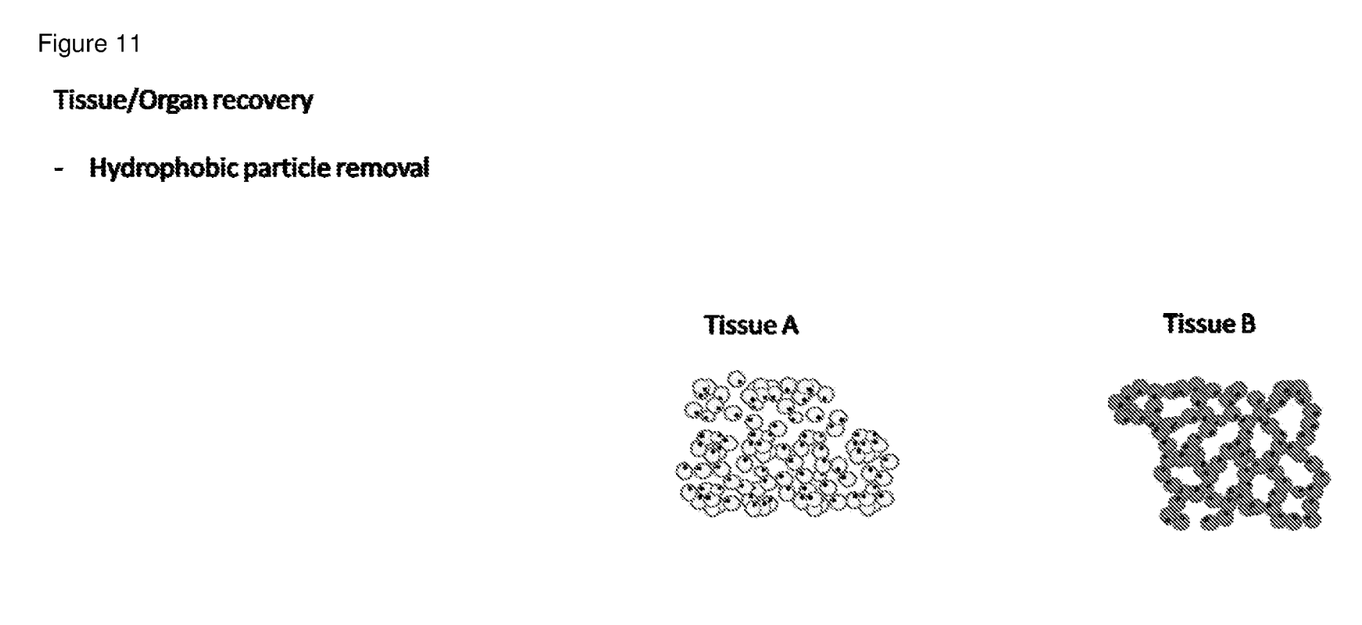
FIG. 11 shows the tissue/organ recovery after hydrophobic particle removal.

Using an electro spray apparatus the core material 1 and the capsule material 3 were released/sprayed into a container over liquid nitrogen vapour. The electro spray apparatus had a concentric delivery tube 4 so that the two materials were delivered together (see FIG. 5). Electrostatics and solvent loss created a core-shell particle structure prior to the capsule passing through a liquid nitrogen vapour. What resulted was a cryo biocapsule powder. The powder of capsules were maintained in a cryo preservation state in liquid nitrogen vapour for storage purposes Adding Capsule to the Substrate (FIG. 6)

In this step a fluidised bed 5 of the biocapsule power was created by suspending the powder in forced flow liquid nitrogen vapour. Samples of the vapour which contained some capsules were then extracted and combined with warm air using a venturi. The warm air caused controlled heating in the delivery tube of the capsules to ensure delivery above 0 C. Using a smooth bore PTFE tubing and PTFE needle, the capsules were then deposited on a temperature controlled PTFE tray 6 and allowed to thaw. Two sets of capsules were deposited both in single layers on distinct areas of the try. In this step, but using a different delivery system, the PTFE capsules 8 (FIG. 7) were added to the tray around the capsules 10.

Exposing the Capsules to the Bioactivating Agents (FIG. 8).

Using a third delivery system a bioactive agent A in an aqueous solution was irrigated over the first group of capsules and an aqueous solution with bioactive agent B was irrigated over the second group of capsules. The process of adding the capsules to the substrate and adding the PTFE and adding the bioactive agent was repeated (FIG. 9) until stacks 12 of the two sets of capsules were created.

The PTFE particles were then removed and culture medium added. Then culture medium was added and the capsules disintegrated leaving just the two groups of differentially activated cells.

See FIG. 10 for the resultant tissue/organ bioreactor, which is then cultured to produce the tissue/organs required (FIG. 11).

The invention claimed is:

1. A multicellular lay-up process, the process comprising the steps of:

a) forming a core material, b) forming a capsule material, c) encapsulating the core with the capsule material, d) adding the capsule to a substrate, and e) exposing the capsule to at least one bioactivating agent, wherein the capsule material comprises a water soluble polymer, a fibrous component, and a solvent, wherein lengths and sizes of the fibrous component are maintained within a predetermined range, and wherein the predetermined range is selected to achieve a desired capsule viscosity.

2. The process according to claim 1, wherein the method comprises forming a plurality of capsules, adding a plurality of capsules to a substrate and exposing the plurality of capsules to at least one bioactivating agent.

3. The process according to claim 1, wherein the core comprises one or more mammalian cells, cell culture medium and a hydrogel.

4. The process according to claim 3, wherein the cells are stem cells.

5. The process according to claim 3, wherein the cell culture medium comprises selective growth medium, growth factor or buffer.

6. The process according to claim 3, wherein the hydrogel comprises any of gelatin, polyethylene glycol, glycerol, alginate, dextran-40, trehalose, or DMSO.

7. The process according to claim 3, wherein the core further comprises at least one bioactivating agent selected from the group consisting of growth factors, growth inhibitors, antimicrobial agents or anti-inflammatory agents.

8. The process according to claim 1, wherein the step of forming the core comprises combining one or more mammalian cells, at least one bioactivating agent, cell culture medium and a hydrogel.

9. The process according to claim 1, wherein the water soluble polymer comprises polyethylene oxide and/or polyethylene glycol.

10. The process according to claim 1, wherein the fibrous component comprises cryomilled bioactive nano fibres, cryosonic milled fibres, or lithographic cut fibres.

11. The process according to claim 10, wherein the fibres comprise natural and/or synthetic polymers.

12. The process according to claim 11, wherein the natural polymers comprise cross-linked collagen or cross-linked hyaluronic acid.

13. The process according to claim 11, wherein the synthetic polymers comprise polylactide glycolic acids, poly lactic acid, poly glycolic acid or polycapralactone.

14. The process according to claim 10, wherein the fibrous component is infused with an enzyme.

15. The process according to claim 10, wherein the fibrous component is infused with an electromagnetic absorber.

16. The process according to claim 1, wherein the solvent comprises any of water or organic solvents.

17. The process according to claim 1, wherein the capsule material further comprises at least one bioactivating agent selected from the group consisting of group consisting of, growth factors, growth inhibitors, antimicrobial agents or anti-inflammatory agents.

18. The process according to claim 1, wherein the step of encapsulating the core with the capsule material comprises electrospraying both the formed cores and the capsule material concentrically in a cryogenically cooled drop tower.

19. The process according to claim 1, wherein the step of adding the capsule to the substrate is performed in an additive manufacturing process.

20. The process according to claim 19, wherein the additive manufacturing process is any of high speed sintering, ink jet printing, poly jet printing, spraying, high resolution deposition, spraying, syringe dispensing, near field electrospray or aero-sol jetting.

21. The process according to claim 19, wherein the adding step further comprises the deposition of a barrier on the substrate.

22. The process according to claim 21, wherein the barrier comprises dry hydrophobic particles.

23. The process according to claim 22, wherein the hydrophobic particles comprise PTFE particles.

24. The process according to claim 22, wherein the deposition of dry hydrophobic particles on the substrate is by any of high speed sintering, ink jet printing, poly jet printing, spraying, high resolution deposition, spraying, syringe dispensing, near field electrospray or aero-sol jetting.

25. The process according to claim 1, wherein the step of exposing the capsule to at least one bioactivating agent comprises irrigating the capsules with an aqueous solution comprising one or more bioactivating agents.

26. The process according to claim 1, wherein the exposing is performed by any of high speed sintering, ink jet printing, poly jet printing, spraying, high resolution deposition or aerosol jetting.

27. The process according to claim 25, wherein the one or more bioactivating agents are selected from the group consisting of group consisting of growth factors, growth inhibitors, antimicrobial agents or anti-inflammatory agents.

28. The process according to claim 1, wherein steps d) and e) are repeated consecutively in order to lay-up a three dimensional array of capsules.

29. The process according to claim 1, wherein capsules formed are between 20 µm and 50 µm in diameter.

30. The process according to claim 1, wherein a plurality of capsules comprising cell types programmed to produce a first tissue type are laid down on the substrate adjacent to a plurality of capsules comprising cell types programmed to produce a second tissue type.

31. The process according to claim 1, wherein the core, capsule material or fibrous component further comprises a near infrared absorber.

32. A multicellular lay-up process, the process comprising the steps of:
  a) forming a core material,
  b) forming a capsule material,
  c) encapsulating the core with the capsule material,
  d) adding the capsule to a substrate, and
  e) exposing the capsule to at least one bioactivating agent,
  wherein the capsule material comprises a water soluble polymer, a fibrous component, and a solvent,
  wherein the core comprises one or more mammalian cells, cell culture medium and a hydrogel,
  wherein the fibrous component comprises cryomilled bioactive nano fibres, and
  wherein at least one of the cryomilled bioactive nano fibres resides entirely within the capsule material.

* * * * *